United States Patent
Suares et al.

(10) Patent No.: US 6,267,974 B1
(45) Date of Patent: Jul. 31, 2001

(54) COSMETIC COMPOSITIONS WITH SENSATE MIXTURES BASED ON ISOPULEGOL

(75) Inventors: Alan Joseph Suares, Cheshire; Alexander Paul Znaiden, Trumbull; Donald Carl Feliciano, Orange; Michele Carrabotta, Fairfield, all of CT (US)

(73) Assignee: Unilever Home & Personal Care USA, Division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/430,071

(22) Filed: Oct. 29, 1999

Related U.S. Application Data

(60) Provisional application No. 60/129,782, filed on Apr. 16, 1999.

(51) Int. Cl.[7] .................. A61K 6/00; A61K 7/00
(52) U.S. Cl. ............................ 424/401; 424/400
(58) Field of Search .................... 424/400, 401; 568/700; 562/589

(56) References Cited

FOREIGN PATENT DOCUMENTS

| 81846/98 | 3/1999 | (AU) . |
| 0 695 509 | 7/1995 | (EP) . |
| 06065023 | 6/1994 | (JP) . |
| 10231238 | 12/1998 | (JP) . |
| 99/13734 | 3/1999 | (WO) . |

*Primary Examiner*—Dameron L. Jones
(74) *Attorney, Agent, or Firm*—Milton L. Honig

(57) ABSTRACT

A sensate composition is provided for imparting a long lasting cooling effect on skin. The composition is a combination of menthyl lactate, isopulegol and menthoxypropanediol, the latter providing a cooling enhancing effect. Cosmetic compositions can be prepared incorporating the sensate composition.

8 Claims, No Drawings

COSMETIC COMPOSITIONS WITH SENSATE MIXTURES BASED ON ISOPULEGOL

This application claims the benefit of U.S. Provisional Application No. 60/129,782, filed Apr. 16, 1999.

BACKGROUND OF THE INVENTION

1. Field of the Invention

The invention concerns cosmetic compositions formulated with nerve receptor skin stimulating terpene mixtures.

2. The Related Art

Somatic sensation enables our bodies to feel, ache and react to temperature changes. The reactions occur when skin sensory receptors throughout the body are stimulated by mechanical, physical or chemical contact Different receptors are responsible for different stimuli; these are categorized as pain, pressure or temperature changes. Special pathways exist for face sensations. The trigeminal nerve is located on the right side of the face. It extends beyond the ear, underneath and branches out towards the cheek area. Properly formulated cosmetic compositions can stimulate the receptors to produce very positive pleasant effects.

One of the oldest stimulants is l-menthol; it imparts a cooling sensation to the skin. Menthol and related terpenes do not really cool through the effect of latent cold. Actually they heighten the perception of cold in the nerve endings in the skin, so that the surface of skin "feels cold". A problem with menthol is that above certain concentrations it causes burning and itching.

Australian Patent Application 81846/98 describes coolant powders imparting a cool/dry feeling to the skin without any burning sensation or harsh odor. The active system is based upon a combination of one or more actives including menthyl lactate and isopulegol.

New cooling agents are continuously being sought which exhibit improved properties. Attributes of interest are odorlessness, tastelessness, relatively low burning sensation and enhanced cooling effects.

Accordingly, it is an object of the present invention to provide a sensate cocktail which when incorporated into a cosmetic composition will enhance pleasant skin sensations while minimizing unpleasant ones.

Another object of the present invention is to provide cosmetic compositions formulated with improved sensate cocktails allowing the compositions to impart rapid and long lasting pleasant sensations to the skin.

These and other objects of the present invention will become more readily apparent from consideration of the following summary and detailed description.

SUMMARY OF THE INVENTION

A sensate composition is provided which includes:

(i) menthyl lactate as a cooling agent;

(ii) isopulegol as a sensory extender; and (iii) menthoxypropanediol as a cooling enhancer.

DETAILED DESCRIPTION OF THE INVENTION

Now it has been discovered that sensory awareness can be stimulated in a highly pleasant manner by a combination of menthyl lactate, isopulegol and menthoxypropanediol. Menthyl lactate operates as a cooling agent, isopulegol interacts therewith as a sensation extender and menthoxypropanediol enhances cooling of the combination. The sensate composition can be applied to a variety of cosmetics. Most particularly they are suitable for skin creams and lotions. However, these sensate compositions will have applicability to dental care (mouthwash, toothpaste, floss), hair care (shampoo, conditioner, styling gels and sprays), shaving products (shaving foam, aftershave lotion), underarm products (antiperspirants and deodorants), personal wash products (toilet bars and body wash liquids), perfume and cologne, lip care products (lipstick and lip balm) all of which are merely illustrative.

Thus, a first necessary component of sensate compositions according to the present invention is that of menthyl lactate. The substance has a molecular weight of 228 and empirical formula of $C_{13}H_{24}O_3$. It is available under the trademark Frescolot Type ML from the Haarmann & Reimer Corporation.

A second necessary component of sensate compositions according to the present invention is that of isopulegol, particularly 1-isopulegol. This material has a chemical name of 5-methyl-2-(1-methylethenyl)-cyclohexanol having a molecular weight of 154 and formula of $C_{10}H_{18}O$. It is available under the trademark Coolact P from Takasago International Corporation, Rockleigh, N.J.

A third necessary component of sensate compositions according to the present invention is that of menthoxypropanediol. Chemically this material is identified as 3-[[5-methyl-2-(1-methylethyl)cyclohexyl]oxy]-1,2-propanediol having molecular weight 230 and empirical formula $C_{13}H_{26}O_3$. This substance is available under the trademark Cooling Agent 10 from the Takasako International Corporation.

Amounts of the isopulegol and menthyl lactate may each range from about 0.0001 to about 2%, preferably from about 0.005 to about 1%, more preferably from about 0.01 to about 0.5%, optimally from about 0.05 to about 0.2% by weight of a cosmetic composition into which the sensate composition is placed. Relative weight ratios of menthyl lactate and isopulegol in the sensate and cosmetic compositions may range from about 1,000:1 to about 1:100, preferably from about 100:1 to about 1:20, more preferably from about 50:1 to about 1:1, optimally from about 20:1 to about 2:1.

Amounts of menthoxypropanediol may range from about 0.0001 to about 2%, preferably from about 0.005 to about 1%, more preferably from about 0.01 to about 0.5%, optimally from about 0.05 to about 0.2% by weight of a cosmetic composition into which the sensate composition is placed. On a relative weight basis, the menthyl lactate and isopulegol combination relative to that of menthoxypropanediol may range from about 1,000:1 to about 1:100, preferably from about 100:1 to about 1:20, more preferably from about 50:1 to about 1:1, optimally from about 20:1 to about 2:1.

Sensate compositions of the present invention may be formulated into cosmetic compositions. Sensate and cosmetic compositions will have substantial amounts of a pharmaceutically acceptable carrier. The carrier may be present in amounts from about 10 to about 99.99%, preferably from about 50 to about 99.9%, optimally from about 98 to about 99% by weight. Since most of the experimentation to date has been conducted on skin care products, pharmaceutically acceptable carriers related to these products will be described below. However, carriers suitable for other types of cosmetics are well known to chemists and the sensate compositions can be appropriately formulated.

By the term "pharmaceutically acceptable carriers" is meant any one or a combination of substances selected from water, polyols, silicone fluids, esters, hydrocarbons and inorganic powders.

Polyols suitable for the present invention may include propylene glycol, dipropylene glycol, polypropylene glycol, polyethylene glycol, sorbitol, hydroxypropyl sorbitol, hexylene glycol, 1,3-butylene glycol, 1,2,6-hexanetriol, glycerin, ethoxylated glycerin, propoxylated glycerin, xylitol and mixtures thereof.

Silicone oils may also be included as carriers in the compositions of this invention. These oils may either be nonvolatile or volatile. The nonvolatile silicone oils useful in the compositions of this invention are exemplified by the polyalkyl siloxanes, polyalkylaryl siloxanes and polyether siloxane copolymers. The essentially nonvolatile polyalkyl siloxanes useful herein include, for example, polydimethyl siloxanes with viscosities of from about 5 to about 100,000 centistokes at 25° C. Such polyalkyl siloxanes include the Viscasil series (sold by General Electric Company) and the Dow Corning 200 series (sold by Dow Corning Corporation). Polyalkylaryl siloxanes include poly (methylphenyl)siloxanes having viscosities of from about 15 to about 65 centistokes at 25° C. These are available, for example, as SF-1075 methylphenyl fluid (sold by General Electric Company) and 556 Cosmetic Grade Fluid (sold by Dow Corning Corporation). Useful polyether siloxane copolymers include, for example, a polyoxyalkylene ether copolymer having a viscosity of about 1200 to 1500 centistokes at 25° C. Such a fluid is available as SF-1066 organosilicone surfactant (sold by General Electric Company). Cetyl dimethicone copolyol and cetyl dimethicone are especially preferred because these materials also function as emulsifiers and emollients. The former material is available from Goldschmidt AG under the trademark Abil EM-90.

Crosslinked siloxane elastomers may also be included as carriers. These substances may normally have an average molecular weight in excess of 10,000, preferably in excess of a million and optimally will range from 10,000 to 20 million. The elastomers may be formed of polyoxyalkylene units or they may be of the "non-emulsifying" variety where these units are absent. These substances are available from Grant Industries Inc., Dow-Corning Corporation and the General Electric Company. They are known under the CTFA names of Crosslinked Stearyl Methyl-Dimethyl Siloxane Copolymer, Polysilicone-11 and Vinyl Dimethicone/Methicone Cross Polymer.

Nonvolatile siloxanes may also be employed. Illustrative of this category are the cyclo polydimethyl siloxane fluids of the formula $((CH_3)_2SiO)_x$, wherein x denotes an integer of from 3 to 6. The cyclic siloxanes will have a boiling point of less than 250° C. and a viscosity at 25° C. of less than 10 centipoise. Cyclomethicone is the common name of such materials. The tetramer and pentamer cyclomethicones are commercially available as DC 244 and DC 344 from the Dow Corning Corporation.

Esters may also be incorporated into the cosmetic compositions as pharmaceutically acceptable carriers. Among the esters are:

(1) Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate. Particularly preferred are $C_{12}$–$C_{15}$ alcohol benzoate esters.

(2) Alkenyl esters of fatty acids having 10 to 20 carbon atoms. Examples thereof include oleyl myristate, oleyl stearate and oleyl oleate.

(3) Ether-esters such as fatty acid esters of ethoxylated fatty alcohols.

(4) Polyhydric alcohol esters. Ethylene glycol mono and di-fatty acid esters, diethylene glycol mono- and di-fatty acid esters, polyethylene glycol (200-6000) mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(5) Wax esters such as beeswax, spermaceti, myristyl myristate, stearyl stearate.

(6) sterols esters, of which cholesterol fatty acid esters are examples thereof.

Hydrocarbons may also be useful as pharmaceutically acceptable carriers. Illustrative of this category are mineral oil, polyalphaolefins, petrolatum isoparaffin, polybutenes and mixtures.

Inorganic powders are useful carriers. Examples include clays (such as Montmorillonite, Hectorite, Laponite and Bentonite), talc, mica, silica, alumina, zeolites, sodium sulfate, sodium bicarbonate, sodium carbonate, calcium sulfate and mixtures thereof.

The carriers may be in liquid, semi-solid (e.g. wax), powder and aerosol forms. Wax systems can be based on silicone chemistry, hydrocarbons and esters. Examples include candellia, ozokerite, behenyl silicones, microcrystalline polyethylene and mixtures thereof.

Aerosol propellants are normally based on volatile hydrocarbons such as propane, butane, isobutane, pentane, isopropane and mixtures thereof. Phillips Petroleum Company is a source of such propellants under trademarks including A31, A32 and A51. Halocarbons including fluorocarbons and dimethyl ether are further widely employed propellants.

Minor adjunct ingredients may also be included in cosmetic compositions of this invention. These ingredients may be selected from preservatives, fragrances, anti-foam agents, opacifiers, colorants and mixtures thereof, each in their effective amounts to accomplish their respective functions.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated.

EXAMPLE 1

A series of taste tests were performed to evaluate the effect of sensates in a simple cosmetic cream. The base formula is outlined in Table I.

TABLE I

Base Formula

| COMPONENT | WEIGHT % |
| --- | --- |
| Cyclomethicone | 36.0 |
| Crosslinked Silicone Elastomer In Cyclomethicone (25% Active) | 24.0 |
| Propylene Glycol | 20.5 |
| Polyethylene Glycol 200 | 10.5 |
| Dimethyl Isosorbide | 2.0 |
| Ascorbic Acid | 5.0 |
| Cetyl Dimethicone Copolyol | 0.8 |
| Water | Balance |

TABLE II

Sensate Components (%) Added to Base Formula

| | SENSATE COMPONENT (WEIGHT %) | | |
|---|---|---|---|
| SAMPLE | Isopulegol | Menthyl Lactate | Menthoxypropanediol |
| A | 1.0 | — | — |
| B | 0.1 | 0.5 | — |
| C | 0.3 | 0.5 | — |
| D | 0.5 | 0.5 | — |
| E | — | 0.5 | 0.5 |
| F | — | 0.5 | — |
| G | — | 0.75 | — |
| H | — | 1.0 | — |
| I | — | 0.1 | 0.1 |
| J | 0.02 | 0.1 | 0.08 |

TABLE III

| SAMPLE | Sensation |
|---|---|
| | SENSATION |
| A | Very Slight Cooling |
| B | Cooling |
| C | Cooling |
| D | Cooling |
| E | Cooling |
| F | Cooling |
| G | Burning |
| H | Burning |
| I | Cooling |
| J | Sustained Cooling |

Isopulegol as shown in Sample A provided only a very slight cooling effect to the cream base formula. Combinations of Isopulegol with Menthyl Lactate were effective at providing a brief cooling. See Sample D. A burning sensation arose as levels of Menthyl Lactate used alone were increased to 0.75%. See Sample G and H. Sustained cooling was obtained by a combination of Menthyl Lactate, Isopulegol and menthoxypropanediol. See Sample J.

EXAMPLE 2

A clinical test was conducted to evaluate the effect of sensates in the base formula outlined under Table I. The test involved a panel of 50 women (ages 35–65). Samples were blind coded. One sample was tested in the morning and the other in the evening. Panelists applied the base formula incorporating sensate components to their face and/or neck. Questionnaires were completed at 10 and 30 minutes respectively after application. Identity of the sensate component compositions are found in Table IV and results recorded in Table V.

TABLE IV

Sensate Components (%) Added to Base Formula

| | SAMPLE (WEIGHT %) | |
|---|---|---|
| SENSATE COMPONENT | A | B |
| Isopulegol | — | 0.02 |
| Menthyl Lactate | 0.5 | 0.1 |
| Menthoxypropanediol | 0.1 | 0.08 |

TABLE V

| | 10 Minute Sensation | | 30 Minute Sensation | |
|---|---|---|---|---|
| | Sample A | Sample B | Sample A | Sample B |
| % Panel Experienced Sensations | 100% (N = 26) | 75% (N = 24) | 100% (N = 26) | 79% (N = 24) |
| % Pleasant Sensations | 57% | 76% | 55% | 81% |
| % Unpleasant Sensations | 41% | 21% | 43% | 16% |

Panelists perceived significantly more pleasant sensations and significantly less unpleasant ones with Sample B. Among the pleasant sensations were those of cooling and tingling. Unpleasant sensations included those of burning, stinging and warming. Extremely high levels of tingling and cooling could also be perceived by the panelists as being unpleasant.

The foregoing description and examples illustrate selected embodiments of the present invention. In light thereof variations and modifications will be suggested to one skilled in the art, all of which are within the spirit and purview of this invention.

What is claimed is:

1. A sensate composition comprising:

(i) menthyl lactate as a cooling agent;
   (ii) isopulegol as a sensory extender; and
   (iii) menthoxypropanediol as a cooling enhancer.

2. The composition according to claim 1 wherein each of the cooling agent, sensory extender and cooling enhancer are present in an amount from about 0.0001 to about 2% by weight.

3. The composition according to claim 2 wherein each of the cooling agent, sensory extender and cooling enhancer are present in an amount from about 0.01 to about 0.5% by weight.

4. The composition according to claim 1 wherein the cooling agent and sensory extender are present in a weight ratio ranging from about 1,000:1 to 1:100.

5. The composition according to claim 4 wherein the weight ratio is from about 100:1 to about 1:20.

6. The composition according to claim 2 wherein a combination of the cooling agent and sensory extender relative to the cooling enhancer are present in a relative weight ratio of about 1000:1 to about 1:100.

7. The composition according to claim 6 wherein the relative weight ratio is from about 50:1 to about 1:1.

8. A cosmetic composition comprising:

(A) a sensate composition comprising:
      (i) menthyl lactate as a cooling agent;
      (ii) isopulegol as a sensory extender; and
      (iii) menthoxypropanediol as a cooling enhancer;
   (B) a pharmaceutically acceptable carrier for delivering the sensate composition.

* * * * *